(12) United States Patent
Hall

(10) Patent No.: US 10,130,732 B2
(45) Date of Patent: Nov. 20, 2018

(54) APPARATUS AND METHOD FOR TREATING WASTE

(75) Inventor: Philip Hall, Westerham (GB)

(73) Assignee: VWP Waste Processing Limited, London (GB)

( * ) Notice: Subject to any disclaimer, the term of this patent is extended or adjusted under 35 U.S.C. 154(b) by 528 days.

(21) Appl. No.: 12/864,825

(22) PCT Filed: Feb. 2, 2009

(86) PCT No.: PCT/GB2009/000276
§ 371 (c)(1),
(2), (4) Date: Apr. 15, 2011

(87) PCT Pub. No.: WO2009/095693
PCT Pub. Date: Aug. 6, 2009

(65) Prior Publication Data
US 2011/0185624 A1    Aug. 4, 2011

(30) Foreign Application Priority Data

Jan. 31, 2008 (GB) .................................. 0801787.3

(51) Int. Cl.
| | |
|---|---|
| C10L 1/00 | (2006.01) |
| A01G 25/16 | (2006.01) |
| B01J 8/00 | (2006.01) |
| C07C 29/74 | (2006.01) |
| A61L 11/00 | (2006.01) |
| B09B 3/00 | (2006.01) |
| C10J 3/00 | (2006.01) |
| C10L 1/02 | (2006.01) |
| C12P 7/08 | (2006.01) |

(52) U.S. Cl.
CPC .............. *A61L 11/00* (2013.01); *B09B 3/00* (2013.01); *B09B 3/0091* (2013.01); *C10J 3/00* (2013.01); *C10L 1/026* (2013.01); *C12P 7/08* (2013.01); *C10G 2300/1011* (2013.01); *C10G 2400/08* (2013.01); *C10J 2300/0916* (2013.01); *C10J 2300/0946* (2013.01); *Y02E 20/12* (2013.01); *Y02E 50/13* (2013.01); *Y02E 50/32* (2013.01); *Y02P 20/145* (2015.11); *Y02P 30/20* (2015.11); *Y02T 50/678* (2013.01); *Y10T 137/86493* (2015.04)

(58) Field of Classification Search
USPC ............ 210/187; 588/318; 264/140; 241/23; 241/19; 137/625; 422/105; 44/307; 568/913
See application file for complete search history.

(56) References Cited

U.S. PATENT DOCUMENTS

| | | |
|---|---|---|
| 4,009,075 A | 2/1977 | Hoge |
| 4,342,830 A | 8/1982 | Holloway |
| 5,079,385 A | 1/1992 | Wu |
| 5,190,226 A * | 3/1993 | Holloway ........................ 241/23 |
| 5,389,114 A | 2/1995 | Forder |
| 5,407,817 A | 4/1995 | Lightsey et al. |
| 5,414,169 A | 5/1995 | Takahashi et al. |
| 5,506,123 A | 4/1996 | Chieffalo et al. |
| 5,556,445 A | 9/1996 | Quinn et al. |
| 5,571,703 A | 11/1996 | Chieffalo et al. |
| 5,655,718 A | 8/1997 | Anderson |
| 5,779,164 A | 7/1998 | Chieffalo et al. |
| 5,849,964 A | 12/1998 | Holighaus et al. |
| 5,968,362 A | 10/1999 | Russo, Jr. |
| 5,975,439 A | 11/1999 | Chieffalo et al. |
| 6,017,475 A * | 1/2000 | Cantrell ......................... 264/140 |
| 6,267,309 B1 | 7/2001 | Chieffalo et al. |
| 6,328,234 B1 | 12/2001 | Saucier et al. |
| 6,357,526 B1 * | 3/2002 | Abdel-Halim et al. ... 166/272.3 |
| 6,391,204 B1 | 5/2002 | Russo, Jr. |
| 6,419,828 B1 | 7/2002 | Russo, Jr. |
| 6,752,337 B2 | 6/2004 | Bonde et al. |
| 6,752,956 B1 | 6/2004 | Vanderwal |
| 7,175,115 B1 * | 2/2007 | Gali ................................ 241/19 |
| 8,445,258 B2 | 5/2013 | Hall |
| 2003/0078552 A1 | 4/2003 | Tepper et al. |
| 2003/0199049 A1 | 10/2003 | Nguyen et al. |
| 2006/0154352 A1 | 7/2006 | Foody et al. |

(Continued)

FOREIGN PATENT DOCUMENTS

| | | | |
|---|---|---|---|
| DE | 3544240 | * | 6/1987 |
| DE | 3544240 A1 | | 6/1987 |

(Continued)

OTHER PUBLICATIONS

DE3544240 Claims; Jun. 1987.*
DE3544240 Description; Jun. 1987.*
Non-Final Office Action from U.S. Appl. No. 12/309,845, dated Apr. 25, 2012.
Office Action from U.S. Appl. No. 12/309,845, dated Nov. 16, 2011.
Office Action from U.S. Appl. No. 12/309,845, dated Apr. 27, 2011.
International Search Report for PCT/GB2009/000276, dated Oct. 22, 2009.

(Continued)

*Primary Examiner* — Prem C Singh
*Assistant Examiner* — Chantel L Graham
(74) *Attorney, Agent, or Firm* — Hamilton, Brook, Smith & Reynolds, P.C.

(57) ABSTRACT

A process and apparatus for recycling municipal domestic waste comprises subjecting the waste to steam at 150° C.-200°. After steam treatment, the resultant material is separated into constituent parts and biomass and/or plastics subjected to further treatment. The further treatment preferably produces bioethanol from the biomass and diesel from the plastics. As an alternative, some or all of the biomass may be gasified in order to produce hydrogen which may, in turn be fed to a fuel cell to produce an electrical output. The bio diesel or bioalcohol can also be used to produce electricity.

11 Claims, 9 Drawing Sheets

(56) References Cited

U.S. PATENT DOCUMENTS

2007/0197852 A1*  8/2007  Wilson et al. ............... 588/318
2009/0314700 A1* 12/2009  Mabuchi ...................... 210/187
2010/0003548 A1   1/2010  Hall
2011/0185624 A1   8/2011  Hall

FOREIGN PATENT DOCUMENTS

| WO | WO09505067    | * | 2/1995 |
| WO | WO 2003/024633 A | | 3/2003 |
| WO | WO03024633    | * | 3/2003 |
| WO | WO 2006/056768 A2 | | 6/2006 |
| WO | WO 2006/095199 | | 9/2006 |
| WO | WO 2008/015424 A2 | | 2/2008 |
| WO | WO 2009/095693 | | 8/2009 |

OTHER PUBLICATIONS

International Preliminary Report on Patentability and Written Opinion for PCT/GB2009/000276, dated Aug. 3, 2010.
International Search Report for PCT/GB2007/002920, dated Jan. 15, 2008.

* cited by examiner (A) ACID TREATMENT VESSEL
    8 HOURS REQUIRED (B) SOLIDS REMOVED (LIGNIN)
    CAN BE USED AS FUEL FOR BOILER (C) SCREW PRESS TO REMOVE ACID (D) FILTER (D) FILTER (E) SUGAR SOLUTION TO FERMINATION VESSELS (F) EXCESS YEAST TO BE PELLITISED FOR FUEL/FERTILISER (G) YEAST RECYCLE (H) DISTILLATION COLUMN (I) STILLAGE CAN BE USED AS FERTILISER

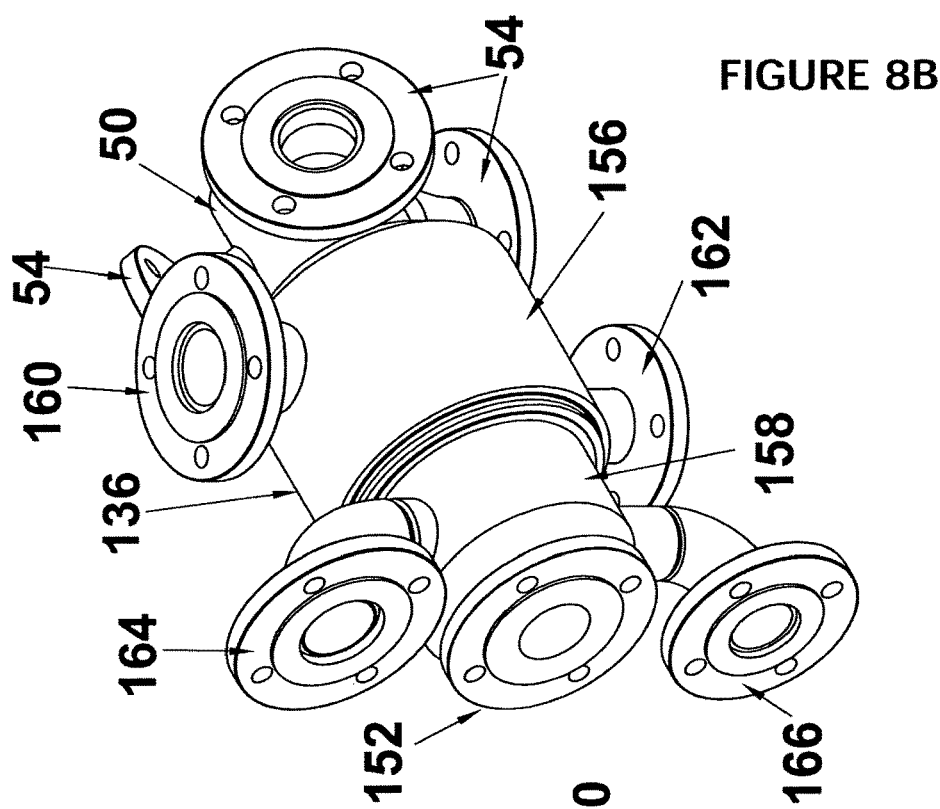
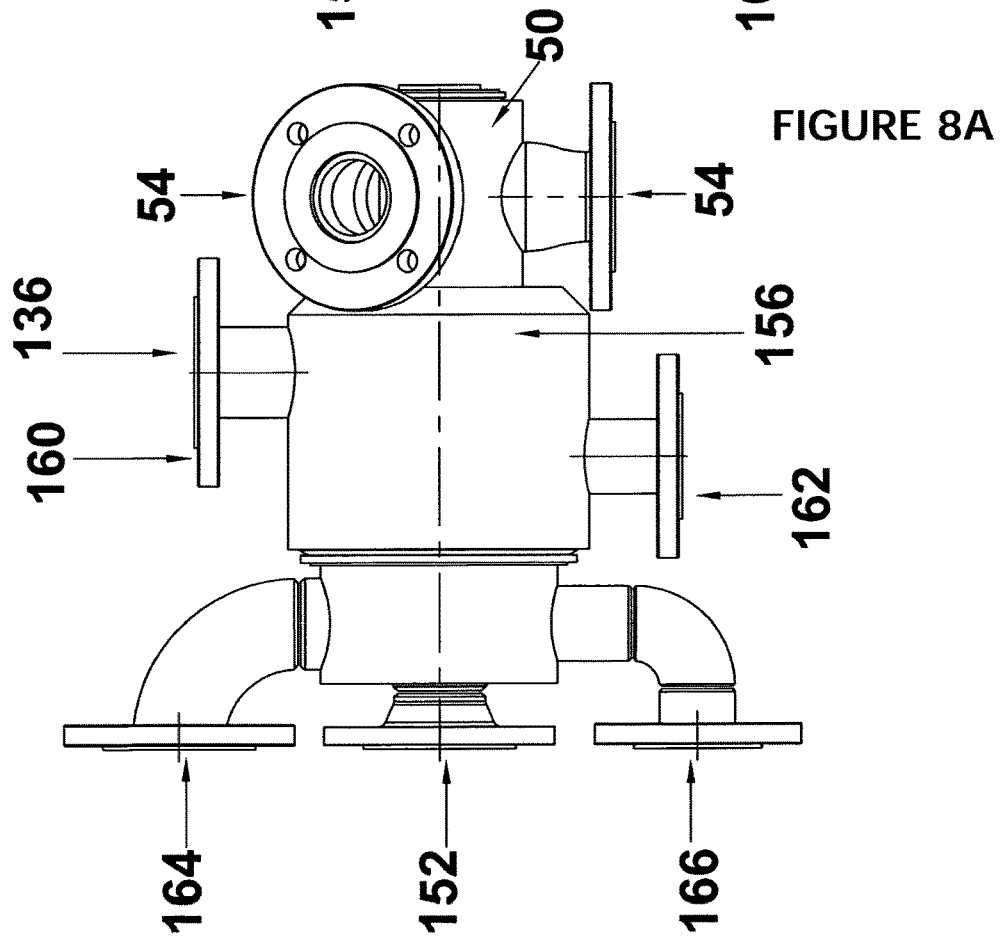

APPARATUS AND METHOD FOR TREATING WASTE

RELATED APPLICATIONS

This application is the U.S. National Stage of International Application No. PCT/GB2009/000276, filed Feb. 2, 2009, which designates the U.S., published in English, and claims priority under 35 U.S.C. §§ 119 or 365(c) to Great Britain Application No. 0801787.3, filed Jan. 31, 2008.

The present invention relates to the recycling of waste material and more particularly to the recycling of municipal domestic waste.

There are a number of ways of dealing with municipal domestic waste, otherwise known as municipal solid waste, but the two most common methods are either by landfill or by incineration. Both these methods have inherent problems associated with them. When utilising landfill, the waste is buried without sorting. It takes up valuable space and renders land unusable for many years. In addition, toxic effluent can leak into the land. Further, suitable locations for landfill sites are becoming increasingly difficult to find.

As far as incineration is concerned, this usually requires the waste to be sorted into combustible and non-combustible waste with the non-combustible waste being sent to a landfill site and the combustible waste burnt. However, the burning of waste usually creates sulphur emissions and requires high unsightly chimneys. Additionally, incinerators are not efficient because they require high energy inputs.

More recently, there have been proposals to dispose of municipal waste by utilising an autoclave charged with the waste material to be treated and supplied with steam from a steam accumulator. An example of this is disclosed in U.S. Pat. No. 5,190,226 where solid waste material is processed at pressure of 4 bar. While these proposals are a more environmentally friendly solution than the two previous common methods described above, they are inefficient as they are batch processes. A continuous process has been developed in e.g. U.S. Pat. No. 6,752,337 but special equipment has been proposed in order to maintain a highly pressurized steam processing unit which is both expensive and hazardous.

The present invention seeks to provide a solution to recycling municipal domestic waste which is both energy efficient and environmentally friendly. The process plant is modular in design and will take unsorted waste and thermally treat it using a continuous steam process. Preferably the system also addresses the problem of odour generated from the plant.

According to the present invention there is provided an apparatus for treating solid waste material comprising a vessel with an inlet for waste to be introduced and an outlet for treated waste, the interior of the vessel having a first zone and a second zone, the apparatus further including a plurality of steam inlets for selectively injecting steam in to the interior of the vessel, a drive arranged to provide relative motion between the steam inlets and the first zone such that only some of the steam inlets are in said first zone at any time, and steam control means arranged to supply steam only to steam inlets in the first zone. This apparatus advantageously directs the steam into the waste material to impart the energy needed to allow the breakdown process, in particular of the organic materials contained in the waste, so that the waste efficiently treated.

It is advantageous for the recycling process to be a continuous process that is easier to achieve when the vessel is an elongate vessel with the inlet at one end and the outlet at the other end. The drive is arranged to rotate the vessel and in this manner transport the material along the vessel whilst also mixing the waste material to ensure that it is fully treated.

Normally, the steam inlets are provided in steam pipes. The steam inlets may be fixed relative to the interior of the vessel. The steam inlets are arranged to inject steam at a temperature of 150° C. to 200° C., and so provide a large amount of kinetic and heat energy directly in to the waste material.

Normally, heating means for heating and/or maintaining the interior to a temperature of 150° C. to 200° C. are provided as this is a simple way to bring the waste material to a temperature where the breakdown process is achieved within a reasonable time frame. The heating means will normally be selected from the group consisting of heated air, an exterior steam jacket and a heating element. It is preferred for the heating means to be only a jacket heated by steam. This is a particular advantageous technique as it is very easy to make the heating controllable, avoid hot-spots in the vessel and is fuel efficient. In this case, the vessel may be separated into a series of sections. The heat input into each section may be individually controllable, for example, so that the material in each zone can be brought to or maintained at a desired temperature. For example, more heat input will be required near the waste inlet as it is necessary to bring the relatively cold waste up to the temperature of the process as quickly as practicable. The area nearest the outlet may be controlled to partially dry the waste material.

The process has the advantage that pressure is not required and so the interior of the vessel is at a pressure under 2 bar, normally under 1.25 bar or even substantially at ambient pressure. This offers great cost savings and increases safety compared to pressured systems.

The treated waste material preferably comprises a biomass containing cellulose material and containing less than 1% sulphur. The biomass is useful in a large number of ways, providing key benefits of the present system.

Normally, a sorting chamber is provided where the treated waste material is separated into plastics, ferrous metals, non-ferrous metals and biomass of cellulose material. Thereafter, the biomass is transferred to a hyperbaric engine or a fuel cell or to a conversion unit for converting the biomass into bio-diesel, an organic alcohol, such as bio-ethanol or bio-butanol, or an aviation fuel. The bio-fuel can be used to power a generator or generators to produce electrical energy or may be used to power other engines (e.g. aircraft engines) or other generators.

According to a second aspect of the present invention there is provided a distributor valve for directing steam from a steam generator or boiler to a steam input, that comprises a valve body having an inlet opening fluidly connectable to the steam generator and a plurality of outlet openings fluidly connectable to the steam input, wherein the valve is arranged so that at any time at least one of the outlet opening is fluidly disconnected from the inlet opening. This component allows the steam to be directed in to the desired channel steam pipe in a simple and robust manner. Normally, the inlet opening is arranged to be fluidly connected to only one outlet opening at a time as normally only one steam pipe will be within the waste material at a time. Of course this can vary depending upon the installation.

The distributor valve can have the inlet opening in fluid connection with one end of a tubular valve member housed in a valve body where the outlet openings are spaced about the circumference of the valve body so as to be individually fluidly connected to the valve member by rotation thereof in the valve body. The distributor valve thus provides an elegant way to implement the steam control means according to the first embodiment of the invention.

The distributor valve according to a preferred embodiment may preferably have the inlet opening in an inlet manifold with a fluid connection extending in an axial direction through a rotatable valve chamber to the valve body. Preferably, the rotatable valve chamber has a steam feed for supplying steam to a heating jacket and a condensate return for receiving condensate from the heating jacket, and the steam feed is fluidly connected to a steam line in the inlet manifold and the condensate return is fluidly connected to a return line in the inlet manifold. This provides a simply way to connect the steam supply to the rotating heating jacket with the rotatable valve chamber rotates with the vessel whilst the rest of the valve remains stationary.

According to a third embodiment of the present invention, there is provided a method for treating waste material comprising the steps of:

a) inputting particulate waste material into a vessel, and
b) treating the particulate waste material with steam at a temperature of 150° C. to 200° C., wherein the vessel is at ambient pressure and/or the steam is injected only in to the particulate waste material. In this way the waste material is broken down in to many useful products in a commercially efficient and environmentally sound manner. The method will normally be provided as a continuous method with waste material being input at the input of the vessel and treated waste material being outlet at the outlet of the vessel.

The method is, of course, preferably carried out using the apparatus of the first and second embodiments of the invention. The treated waste material will advantageously comprise a biomass of cellulose, plastics, ferrous metals and non-ferrous metals. The biomass formed by the method is particular advantageous as it is suitable to be further treated to form: bio-diesel, fuel for a fuel cell, bio-alcohol e.g. bio-ethanol, a substitute fossil fuel, or an aviation fuel, possibly mixed with bio-alcohol.

In order that the present invention is more readily understood, embodiments thereof will now be described by way of example, with reference to the accompanying drawings in which:

FIG. 8 shows a second distributor valve of a second preferred embodiment of the present invention in plan (FIG. 8A) and perspective (FIG. 8B) views.

Figure 1:
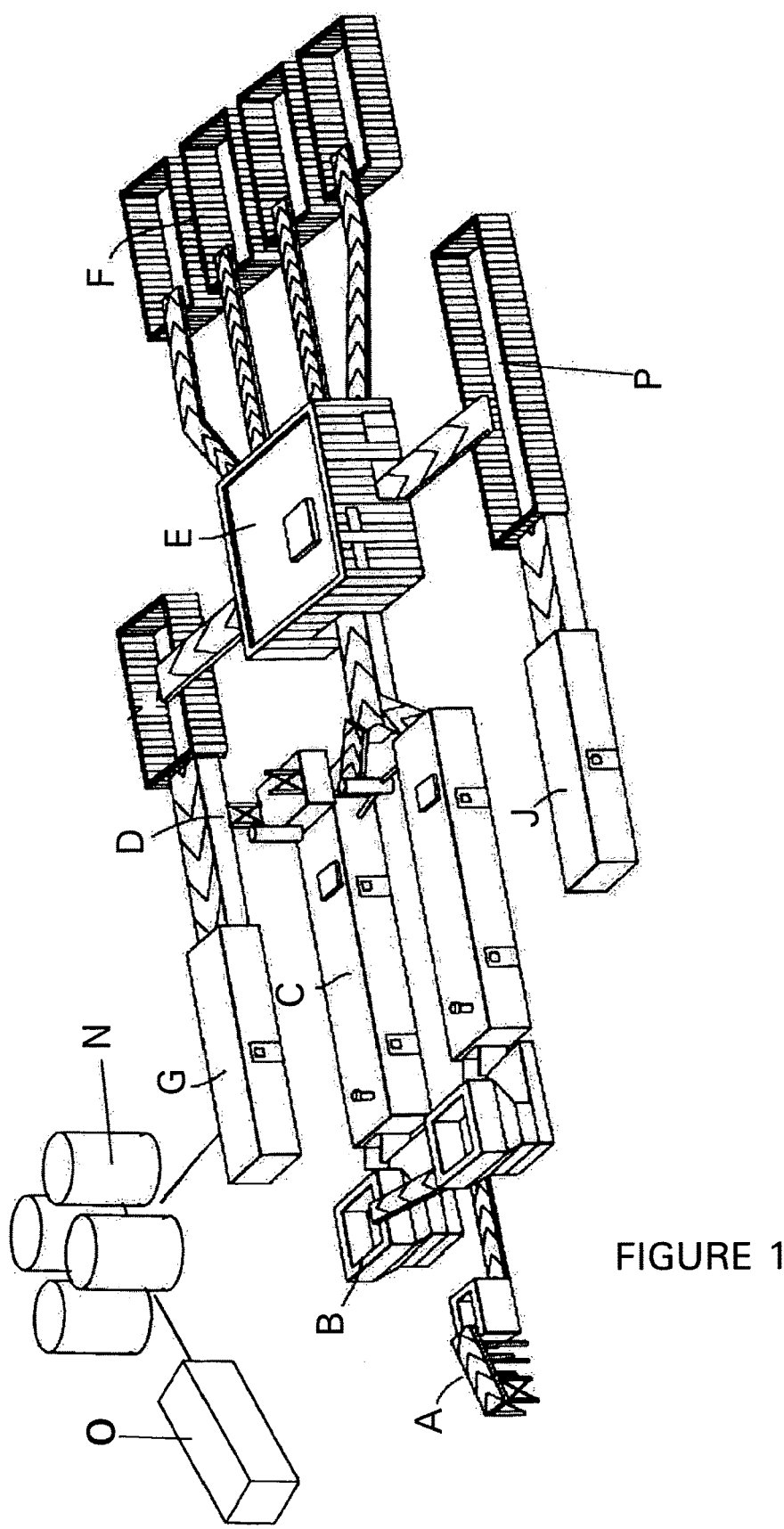
FIG. 1 shows a diagrammatic representation of process plant according to the present invention.

Referring to FIG. 1, this shows diagrammatically the preferred process plant according to the present invention. Refuse vehicles bring municipal domestic waste to a transfer site A where the raw waste, without sorting, is continuously fed via mechanical shredding unit B to a steam treatment unit C. In FIG. 1, there are two steam treatment units operating in parallel each with its own hopper for storing shredded waste prior to it being fed into the unit. By the term 'raw' is meant that no additional matter such as chemicals and/or water is added to the waste prior to being fed into the steam treatment unit(s).

Figure 4A:
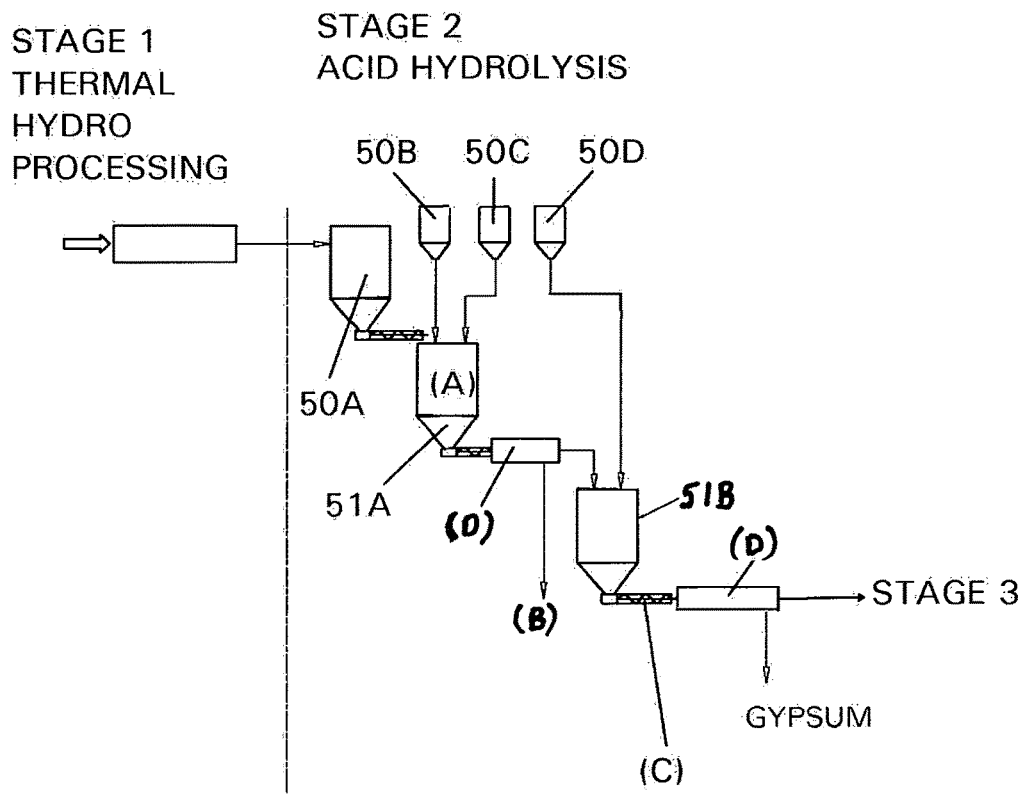
FIG. 4 is a schematic diagram representing the production of ethanol from the system according to the present invention.
Figure 4B:
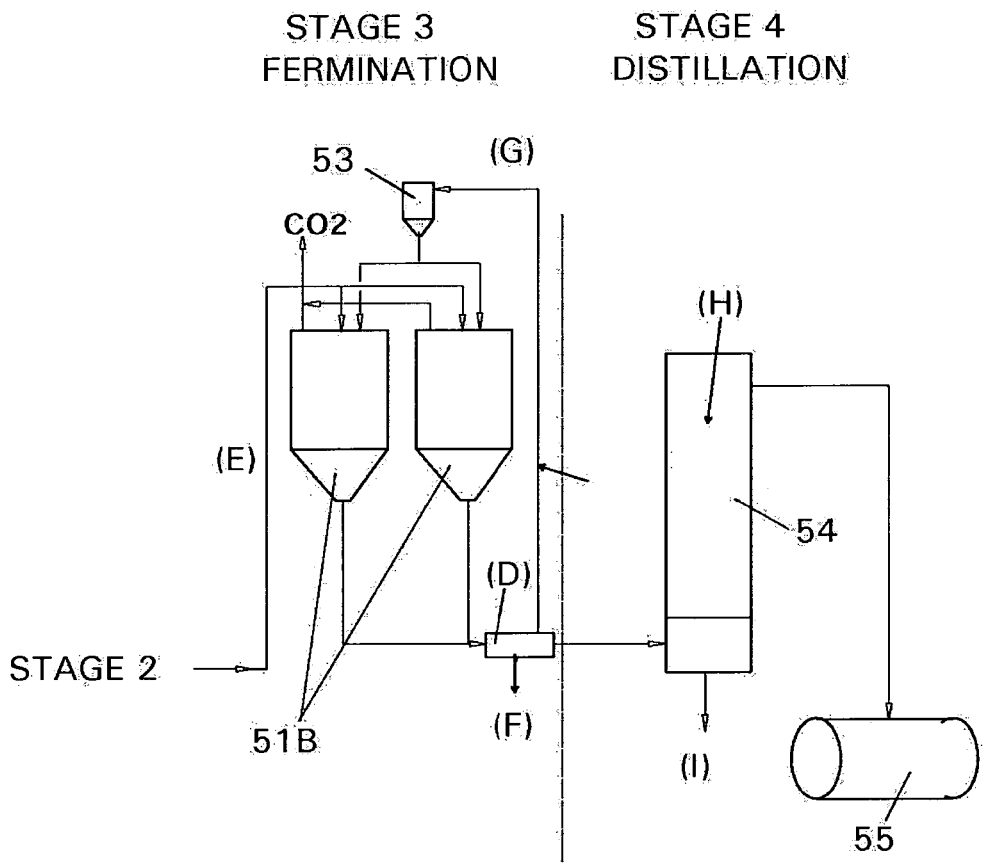
Figure 5:
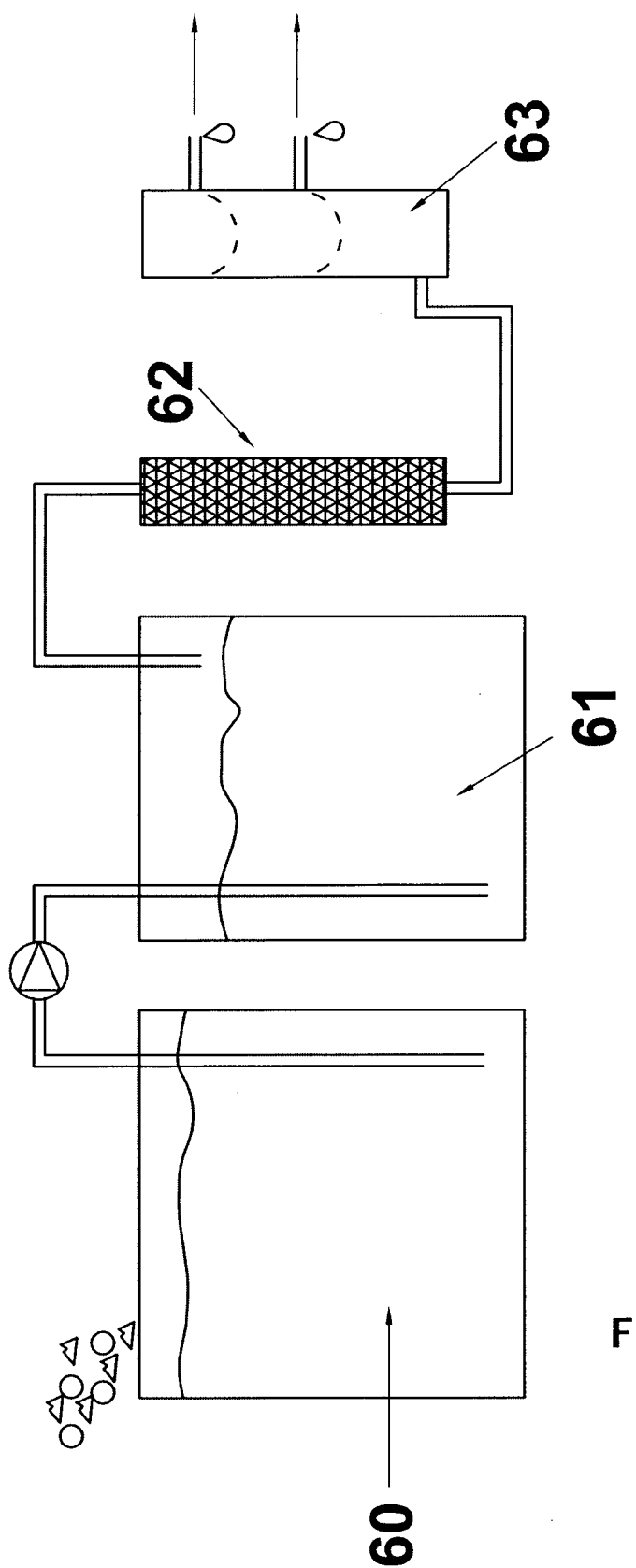
FIG. 5 is a schematic diagram representing the production of bio-diesel from the system according to the present invention.

The steam treatment unit C is operated such that the waste is treated for approximately 45 to 60 minutes and the treated waste is then separated at a separating stage E into different categories such as raw biomass or cellulose, plastics, ferrous metal, non-ferrous metal, textiles and other residues and the material. The techniques and variations for separating the mixed output from the steam treatment unit C are well-known to those skilled in the art. Utilising these techniques, less than 10% by volume of the initial waste is actually sent to landfill and the other sorted waste can be recycled. There is an up to 60% reduction in the volume of waste. The raw biomass and plastics receives further processing indicated by units G and H and/or it may be stored, dried and then fed to a gas converter unit (gasifier—not shown), or treated to input into a fuel cell (not shown) which may be used to generate electricity. The biomass may also be treated to form the fuel for a hyerbaric engine (not shown) or be directed to N to be used in bio-fuel production e.g. bio-ethanol, bio-butanol or bio-diesel as described in greater detail below. The bio-fuel can be used as the fuel of an electrical generator if desired. If all the fuel produced by a fully functioning plant as shown in FIG. 1 was used in this latter fashion, the generators should produce between 6 MW and 20 MW of electricity. FIGS. 4 and 5 show alternative processing for the cellulose material or part of it. The other sorted materials are stored as indicated at F. The plastics material sorted from unit P can be directed to a plastic recovery unit J.

By its very nature, the waste material will exude unpleasant odours at both the inlet to and outlet from the steam processing unit C. For this reason, it is proposed to extract the air from the steam treatment unit and treat it with an odour removal process, as indicated by D in FIG. 1, such as that described in International application No. PCT/GB2006/000888 where the air is treated by ozone generated utilising ultraviolet light. A feature of this technique is that if sufficient ozone is generated and kept in contact with the air to be treated for a sufficient period of time, substantial reductions in odour are achieved. This does require, however, that additional ultraviolet light be provided at a different wavelength to that used to create the ozone in order to ensure that no active ozone is present in the air discharged to atmosphere from the process. The steam processing unit C is not sealed for pressure containment, but normally screening or curtaining will be adopted to allow the gases and steam to exit the steam processing unit C via the desired pathways.

Figure 2:
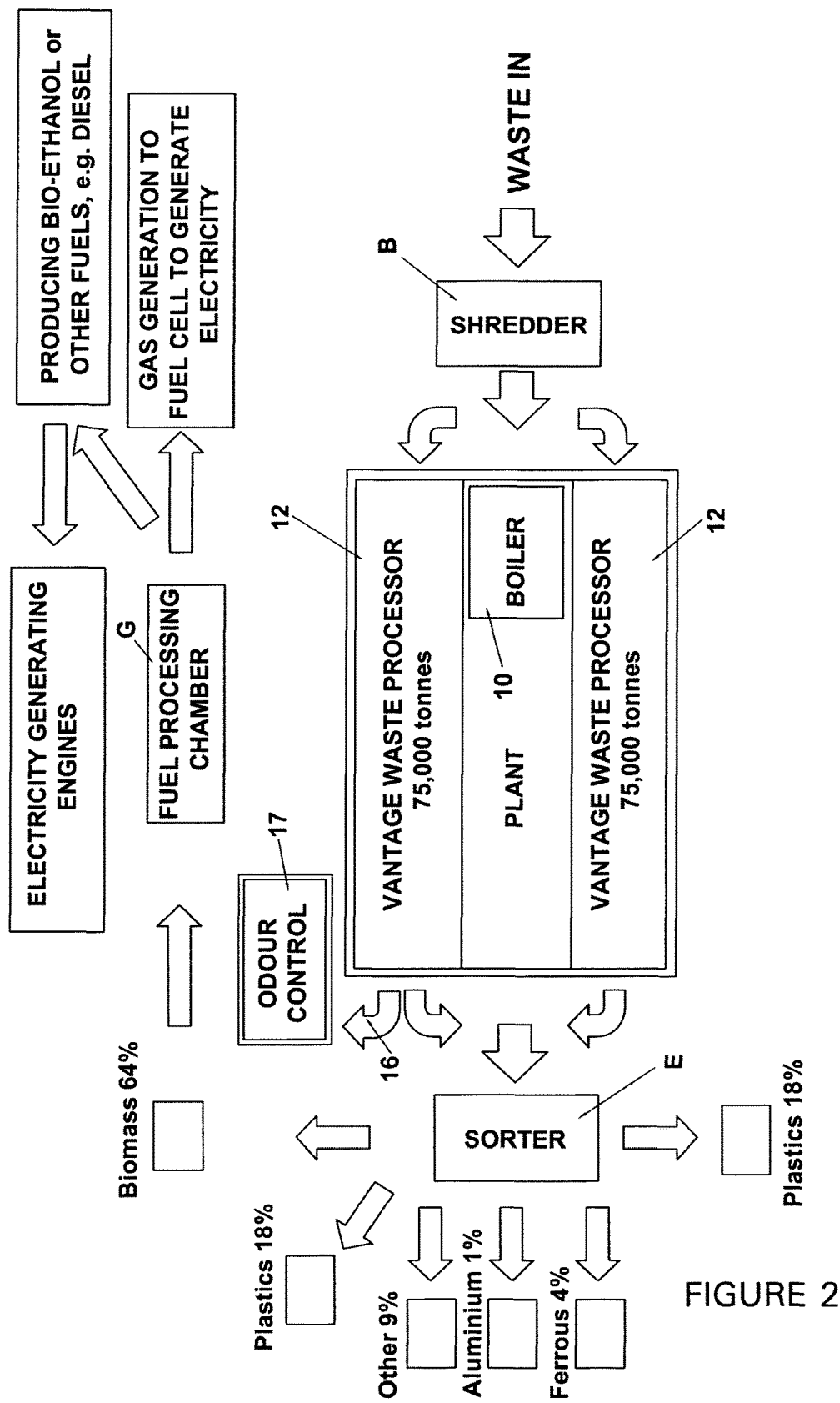
FIG. 2 is a flow chart of the basic process utilized by the present invention.

Referring to FIG. 2, steam is generated in a boiler arrangement 10 which provides steam at an elevated pressure, normally between 12 and 15 bar, and in the illustrated embodiment 14 bar, and has a preferred temperature, of between 190° C. and 200° C. which is fed to a steam treatment section 12 which may include one or more individual units operating in parallel. Waste from the reception and feed area represented by the block B is fed to the steam treatment plant at the temperature and pressure indicated below. Treated waste is then conveyed to a sorter E.

Additionally, any steam escaping from the steam treatment unit is captured by a ducted system 16 and fed to an odour treatment unit 17 where it is treated as described above prior to being vented to atmosphere.

Figure 3:
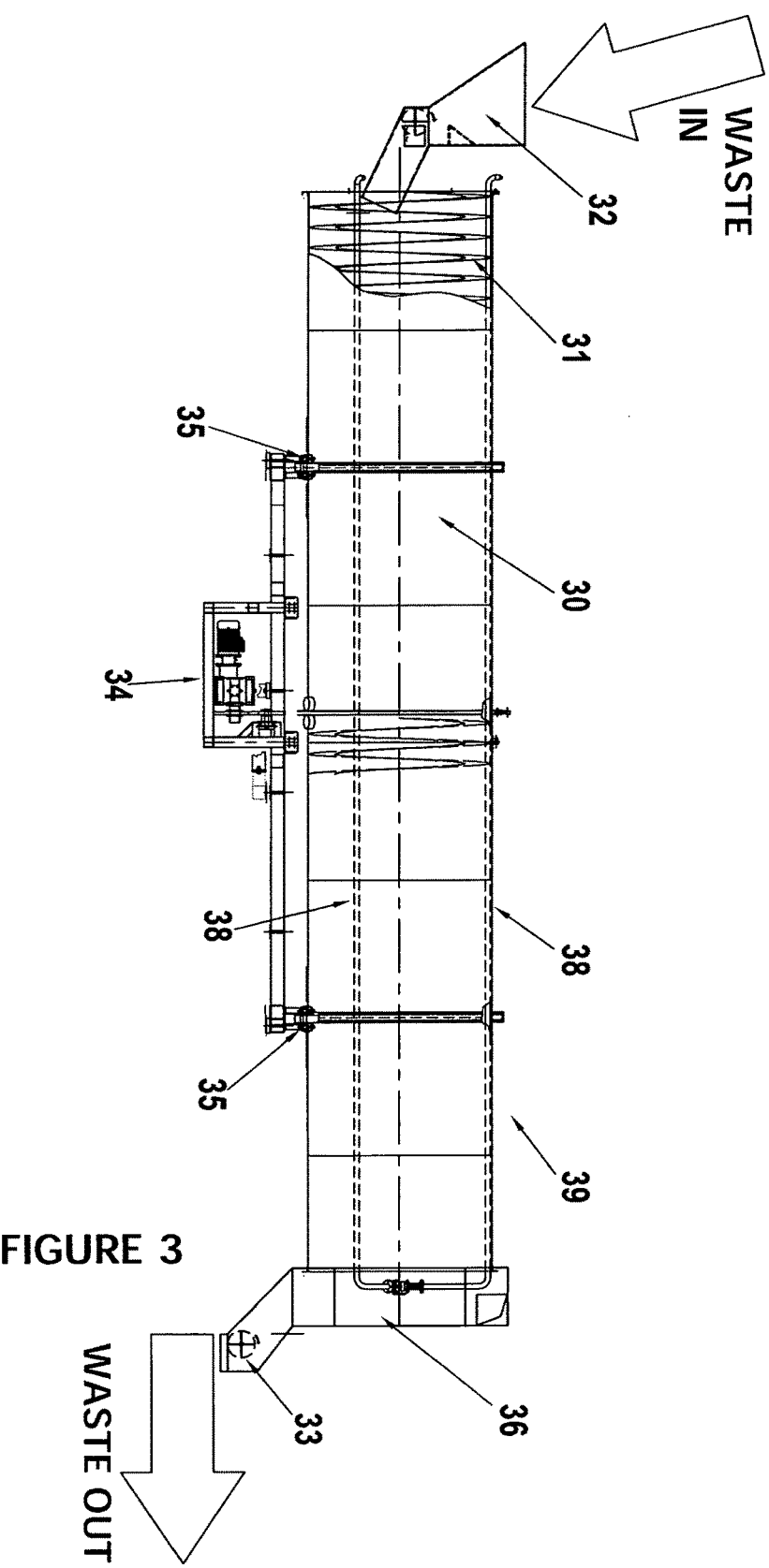
FIG. 3 is a schematic diagram of a first a steam treatment unit used in a first embodiment of the present invention.
Figure 7:
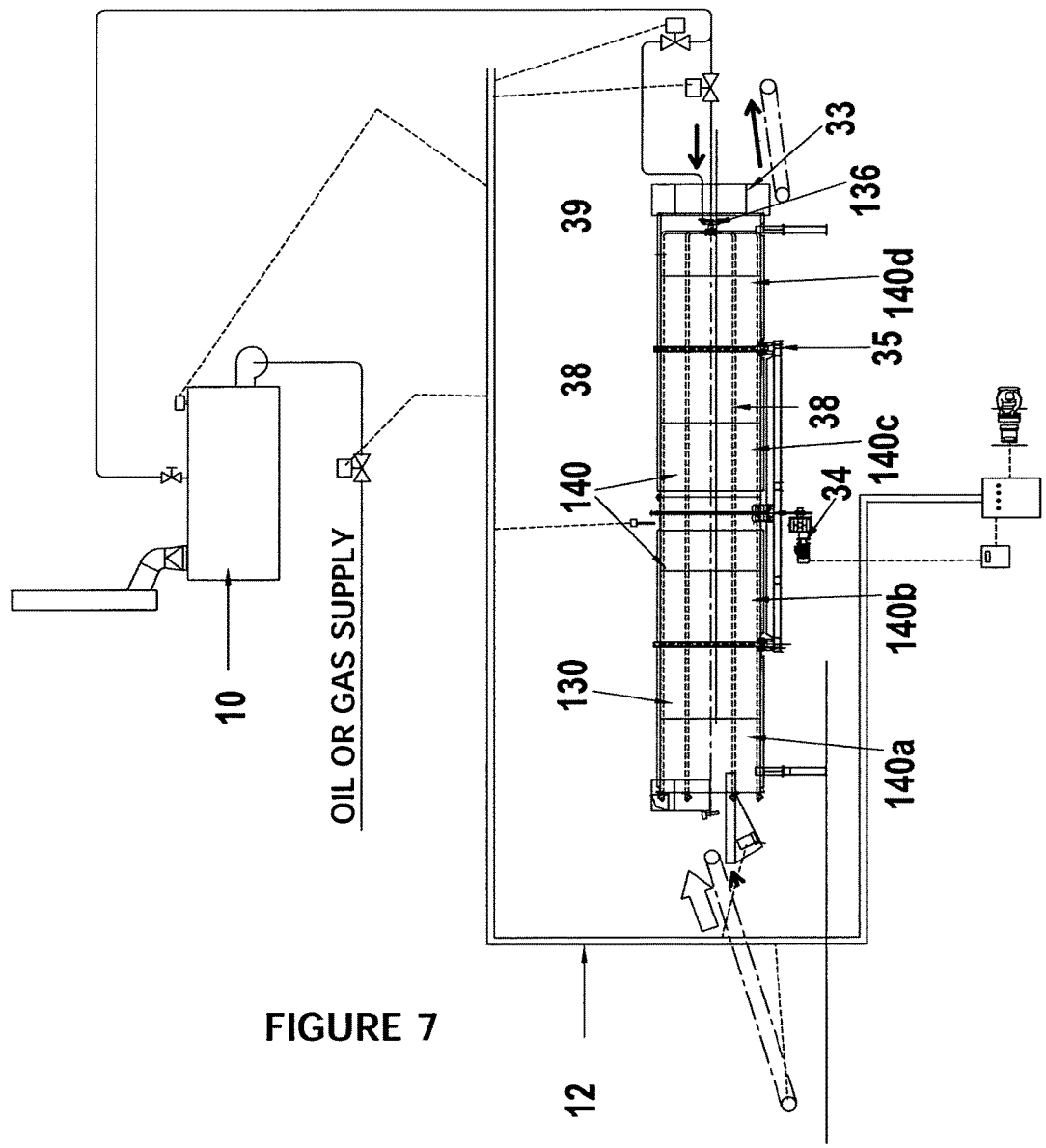
FIG. 7 is a schematic diagram of a steam treatment unit used in the present invention.

Referring now to FIG. 3, this shows in more detail one form of the steam treatment unit C of the plant. It comprises an elongate vessel 30 which is provided with a conveyor arrangement 31 for moving waste material from an inlet 32 to an outlet 33. The inlet 32 is shown as a hopper-type device in FIG. 3 though a vibrating conveyor as shown in FIG. 7, or other device, could also be used.

The preferred arrangement, of vessel 30 is to make it a rotating drum-type of conveyor the internal surface of which is fitted with one or more continuous helical blades. The time during which the waste material is treated is, of course, a function of conveyor rotational speed and conveyor length and these are adjusted such that the waste is treated for approximately 45 to 60 minutes.

The interior of the vessel is maintained at a temperature of between 150° C. and 200° C., preferably with a lower temperature of 160° C. and, independently, an upper temperature of 180° C. At temperatures lower than 150° C. the conversion rate for the breakdown of the waste material is very slow and it would be necessary to maintain the waste in the vessel 30 for a period of time which were commercially unacceptable. At temperature of 200° C., plastic materials in the waste are likely to start decomposing, e.g. by pyrolysis which generates toxic gases and other toxic compounds which would greatly complicate the processing and so it is important to avoid or minimise the generation of such toxic material.

The waste is treated by using steam injected into the vessel 30 by means of pipes 35. The injected steam is preferably at 150° C.-180° C. but may be at a temperature up to 200° C. The steam is injected in to the waste material in the chamber 30 at a pressure in the range of 5 to 12 bar, preferably 10 bar. Although the steam can be injected throughout the chamber, it is preferred for the steam to be directed solely into the waste material. At the pressures and temperatures used in the process, the steam provides a relatively high amount of kinetic energy which is efficiently transferred in to the waste material when the steam is injected thereinto. The injected steam thus efficiently breaks down the waste materials. In particular the injected steam efficiently processes organic material in the waste so that it converts into a biomass of cellulose material containing little or no sulphur.

In addition to the inlet and outlet 32, 33, the chamber 30 or drum may be provided with a bottom hopper for the collection and removal of any bottom material resulting from the steam processing. Also, a gas vent may be provided for removal of gasses resulting from the process. These gasses can be cleaned and separated so that useful hydrocarbons can be used in other parts of the plant and/or have any heat energy removed from them and reintroduced into the process.

When the overall processing plant is being used for general waste, it may be necessary to pre-process the waste to render it more uniform in size by means of a shredding process prior to feeding it to the inlet to the unit. This will ensure that there are no blockages at the inlet to the treatment unit and provide a more consistent product. However, for the invention, it is only necessary for the material to be in pieces, i.e. particulate form.

The construction of a steam processing unit C (FIG. 1) will now be described in more detail with reference to FIG. 3. The steam processing unit C comprises a rotatable drum 30 horizontally mounted on rollers 35 and arranged to be driven by a chain (not shown) by a motor 34. The drum 30 is of uniform cross-section area throughout its length and is provided on its internal surface with a number of spaced blades. The blades may be formed from a single continuous helical screw member or a number of part-helical blades extending in a helical configuration substantially along the length of the drum 31. If necessary, axially disposed blades may be provided between the turns of helical sections in order to promote lifting and tumbling of the material when loaded into the vessel.

Figure 6:
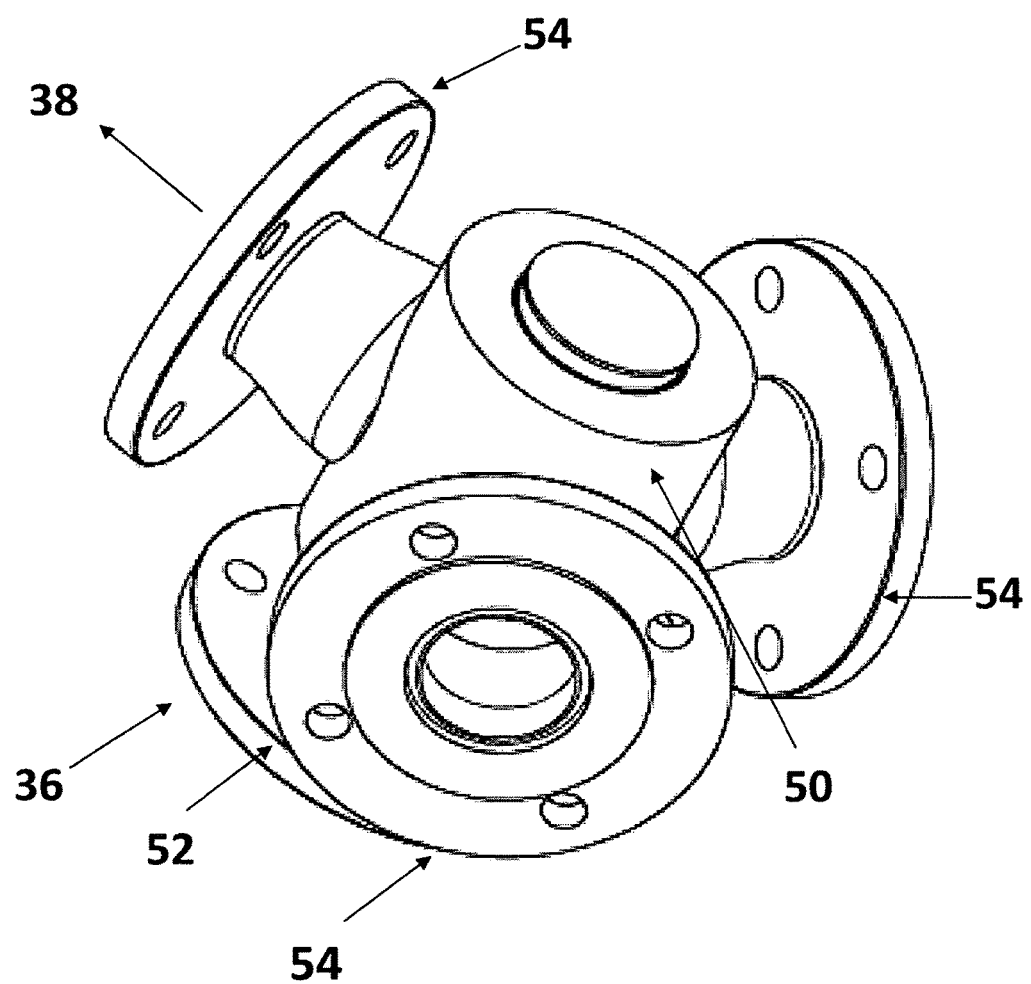
FIG. 6 is a diagram of a distributor valve of a first embodiment of the present invention.

Steam is introduced into the vessel 30 by a plurality of pipes 38 extending along the length of the vessel, in this case these are provided on the internal surfaces of the vessel 30 and have apertures centralized in each pitch centre. One end of each pipe 38 is closed and the other end is attached to distributor valve 36. Distributor valve 36 is located on the central axis of the vessel. The valve 36 is fluidly connected to a supply pipe from a source of steam. The distributor valve 36 is shown in detail in FIG. 6. The distributor valve 36 comprises a valve inlet 52 located on valve housing 50 through which from the steam boiler 10 is input. The valve housing 50 also has 3 valve outlets 54 each connected to a respective steam pipe 38. The distributor valve 36 can simply fluidly connect the steam supply to each of the steam pipes 38. However, it is preferred for the valve 36 to supply steam to each steam pipe 38 in turn as the vessel 30 rotates. As explained in more detail below, the vessel 30 is supplied with waste at a predetermined rate so that the waste only fills the vessel to a known level. This level separates the vessel 30 into two zones, the first zone mainly filled with the waste material, the second zone being largely empty of waste. Each steam pipe 38 is fixed to the vessel 30 and thus moves between the two zones as the vessel 30 rotates. The valve 36 has internal ports inside housing 50 fluidly individually connecting each of the steam outlets 54 so that only the steam pipe(s) 38 in the first zone are connected to the steam supply at any given time. In this way steam is only injected in to the waste material.

The end of the vessel is located within a shroud which serves to contain the steam within the vessel and also serves as the outlet for treated waste.

When the vessel 30 is rotated, in use, at 1-2 revs/min, steam is injected into the material when it overlies one of the pipes 38 as described in more detail above.

The interior of the vessel 30 will normally be heated to 150° C. to 200° C., preferably a lower value of 160° C. and independently an upper value of 180° C. by a heating means. The heating means may be air that can be heated and the hot air blown in to the chamber. Preferably, a heating element in the vessel or wrapped around the vessel 30 could be used. Preferably, the vessel 30 can be have a steam jacket thereabout, in which case the jacket can be formed between layers of the material from which the vessel is made. The same steam boilers 10 can be used or alternatively a separate source of steam can be used. The steam fed to the steam jacket will be at a temperature and pressure to achieve the desired temperature in the vessel.

FIG. 7 shows a preferred version of the steam treatment unit C of the plant. The steam treatment unit C is generally similar to the steam treatment unit C shown in FIG. 3 and the same reference numerals are used to designate parts of the unit that are the same.

Waste is fed into the vessel 130 on a vibrating conveyor 132. The conveyor vibrates in order to keep the waste material from clumping. The waste material is fed on to the vibrating conveyor from a standard conveyor 133. The waste material is transferred to outlet 33 by the conveyor means 31 in the vessel 130. The interior of the vessel 130 is the same as the interior of the vessel 30 with blades provided to transfer the waste material as the vessel rotates.

The principle difference between the vessel 30 and the vessel 130 is that the steam is not fed in to the vessel 130 in order to heat the chamber and waste material to processing temperature, though steam is still used to treat the waste material through the pipes 38. The chamber and waste material is now heated via a heated jacket 140 surrounding the whole vessel 130 and explained in more detail below.

The vessel 130 has heating jacket 140 encases the vessel 130. The heating jacket 140 comprising a network of pipes which are fed steam from the valve 136. In order to heat the vessel 130 and waste material quickly to the desired processing temperature of 150° C. to 200° C. the heating jacket is divided in to four sections 140a-d, extending from the inlet section 140a via the first processing section 140b, the second processing section 140c to the outlet section 140d. The greatest demand for heat is in the inlet section 140a where the waste material must be brought from ambient temperature to the processing temperature in the least practical time and typically 40-60% of the energy is required in the inlet section 140a. As the waste traverses the vessel 130, the waste retains more heat energy and so less energy is required to keep the waste material at a suitable processing temperature. For example, in the processing sections 140b, 140c around 55-30% of the energy is required. In the final outlet section 140d, the waste material is also partially dried to a typical moisture content of 20 to 40%.

Heat is supplied to the heating jacket in the form of steam from the same steam boiler used to supply the steam injected in to the waste material. An efficient way to fluidly connect the heating jacket 140 to the boiler is to use a revised design of the distributor valve 136 as shown in FIG. 8. The distributor valve 136 shown in FIG. 8 is generally similar to the distributor valve 36 shown in FIG. 6 and the same reference numerals are used to designate parts of the unit that are the same.

The distributor valve 136 comprises a steam inlet 152 located on an inlet manifold 158. A fluid connection extends through the interior of a valve chamber 156 to the valve housing 50. The valve chamber 156 is rotatable around the centre axis of the vessel 130 but the inlet manifold 158 and valve housing 50 are stationary. The valve chamber 156 has a steam feed 160 feeding the steam to the heating jacket 140 and a condensate return 162 returning condensate from the heating jacket 140. The rotation from the vessel 130 is coupled to the valve chamber 156 via the steam feed 160 and condensate return 162. The inlet manifold 158 also includes a steam line 164 fluidly connected to the steam feed 160 and a return line 166 fluidly connected to the condensate return 162. Internally, the valve chamber is divided into a first annular space connecting the steam feed 160 to the steam line 164 via an annular space in the inlet manifold 156 and a second annular space connecting the return line 166 to the condensate return 162 via another annular space in the inlet manifold 152. The annular spaces all surround the fluid connection between the steam inlet 152 and the valve housing 50. The first and second annular spaces are fluidly separate from one another. Of course the precise internal configuration of the valve can be varied.

To ensure efficient condensate removal each section 140a-d will incorporate at least one steam trap. The steam trap is designed to prevent the inclusion of live steam to be returned to the boiler with the condensate. The steam trap shall in turn be connected to a condensate reservoir. This shall typically comprise a large bore pipe which shall be positioned around the circumference of the drum. Condensate shall drain into the reservoir at various points around the circumference with the condensate rotating with the drum until it is allowed to drain into the removal pipe work when the outlet port reaches the bottom of the rotating cycle.

The basic process is shown in FIG. 2. The process creates a large volume of biomass mainly comprising cellulose material. Advantageously, it is possible to utilise the biomass as a fuel for the process plant itself or as a separate product such as bio-ethanol, bio-butanol or other derived product as described in more detail below. Cellulose fibre contained in the biomass which is output from the steam treatment unit has a gross calorific value of 11 MJ/kg which provides three kW of energy. If dried, the gross calorific value of the cellulose material increases to 17 to 18 MJ/kg. This biomass contains virtually no sulphur and thus, when burnt, is much cleaner than fossil fuel and so used as a fossil fuel substitute.

The cellulose fibre could be sold as a commodity or it could be sent to a biomass gasifier which produces gaseous fuel from this cellulose biomass as described in more detail below. This gaseous fuel could then be further processed in order to provide the input hydrogen for a fuel cell to produce direct current electrical output. Alternatively, the cellulose material could be further processed as shown in FIGS. 4 and 5 to produce bio-ethanol, bio-butanol, bio-diesel and aviation fuel prior to any solid residue being processed as described above.

Turning now to FIGS. 4 and 5, this shows how biomass and/or plastics produced from the output from the steam processing may be handled to produce bio-ethanol/diesel shown generally in FIG. 1 as units N and J respectively.

Dealing firstly with the cellulose material and as indicated in FIG. 4, the biomass from the steam treatment unit of FIG. 1 has been treated to sanitise the material by substantially halting undesirable anaerobic processes and to be more amenable to hydrolysis as shown generally in stage 1 of FIG. 4. In stage 2 shown in FIG. 4, the biomass is stored in biomass silo 50a for about 8 hours. The biomass is then fed to acid treatment vessel 51a and then treated with sulphuric acid, from acid tank 50b, to undergo acid hydrolysis for about 8 hours. Water is provided from a water tank 50c. The product is then filtered and solids removed (lignin) which can be used as fuel for the boiler of the steam treatment plant. Lime from lime storage hopper 50d is added to neutralise the liquid product in acid removal neutralising vessel 51b and further purified and filtered. Hydrolysis is used to break down the solid biomass into cellulose and hemicellulose as these are the principle sugars contained in the biomass. The process also, advantageously, removes the heavy metals. As mentioned above, acid hydrolysis also acts to supply fuel to the boiler in the form of lignin which forms the principle non-hydrolysable residues.

In an alternative stage 1, not shown, rather than acid hydrolysis, the biomass is loaded into a tank where it is broken up by adding an enzyme such as aspergillums enzyme or using cellulolytic micro-organisms and a nutrient. Additional water may be added. At this stage, active ozone from a generator may also be injected into the tank. The resultant mass is allowed to stand for a period of time and then the liquid is drawn off which will contain soluble sugars.

In either case, the liquid is then fed to fermentation vessels 52 where fermentation takes place by adding to the liquid adding yeast from a yeast silo 53. The yeast will normally be *saccharomyces cerevisiae*, which may be recycled as shown. Fermentation will normally take around 72 hours. The result is a liquid containing ethanol and other products and this liquid is then fed to stage 4, comprising a distillation column 54 in order to distil off and collect the ethanol in ethanol storage tank 55. Distillation will take the fermented mxture which will comprise a 12-14% ethanol solution and concentrate the mixture up to about 99% ethanol or higher. This is achieved in two stages, the first being a conventional distillation which will result in a solution of about 94% ethanol and the remainder of the water will be removed by a molecular sieve.

The process illustrated in FIG. 4 will often be provided in a series of parallel units so that the process can be run continuously.

The ethanol or other bio-fuel produced by the method and apparatus of the present invention can be used in normal fashion if desired. Advantageously, the fuel can be used to power directly generators as shown in FIG. 2 located on site so as to avoid any wastage involved in transport or the like. The generators shown as will normally comprises several engines of 1.5 to 3 MW as available from major engine manufacturer such as Cummins, Perkin, Caterpillar and General Electric. These can be easily modified to run on biofuels. A fully functioning plant as shown in FIG. 1 should produce sufficient fuel to generate about 6 MW to 15 MW of electricity. The output and the generator can be varied depending on the particular installation.

Turning now to the plastics material reclaimed from the steam processing, as shown in FIG. 5, this is fed to a tank 60 where a solvent is added and the resultant mixture left to stand in an evaporation tank 61. After a suitable amount of time, the resultant vapour is drawn off through a zeolite catalyst 62 and then distilled in a distillation tower 63 to collect diesel. If desired, ozone may also be injected into the tank 60.

The ozone injected into the tanks 51 and 60 may be generated in the same fashion as is used for removing odours from the air in the vicinity of the steam processing unit and generator. The ozone may be supplied from a separate generator or generators. Additionally, if needed, the air in the vicinity of the ethanol process may be subjected to ozone treatment to remove any excess active ozone remaining in the tanks 51 and 60.

The present invention handles municipal solid waste and various other organic materials requiring recycling and recovery. These materials have high biomass content and are prone to contamination by micro-organisms present in the natural environment that can result in unwanted fermentation and degradation reactions. It is important to control these organisms to minimise contamination of the feedstock entering the subsequent biomass conversion stages especially those relying on fermentation.

It is also preferable to coat the interiors of some or all of the tanks 51, 52, 60, 61 with an anti-microbial agent. Preferably the agent is one which is non-leaching and non-volatile and is not consumed by microorganisms. Particularly suitable agents are those which are capable of being coated on a surface.

Suitable antimicrobial formulations are those which include, as an active ingredient, a quaternary ammonium salt, preferably a chloride or bromide salt. The nitrogen atom of the salt is preferably substituted by a silane group, preferably a trialkyloxysilane group, most preferably a trimethyloxysilane group. Most preferably the silane group is attached to the nitrogen atom of the salt via a propyl group. The nitrogen atom of the salt is preferably also substituted by three other alkyl groups, at least one of which is preferably methyl, and at least one of which is preferably $C_8$ to $C_{20}$ alkyl. Thus, the preferred compounds have the following general structure:

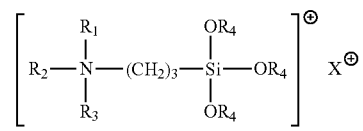

Where:
$R_1$ is methyl;
$R_2$ is methyl or $C_8$ to $C_{20}$ alkyl, preferably methyl;
$R_3$ is $C_8$ to $C_{20}$ alkyl, preferably tetradecyl or octadecyl;
$R_4$ is $C_1$-$C_4$ alkyl, preferably methyl; and
X is chlorine bromine, preferably chlorine.

One example of a useful antimicrobial agent incorporates 3-(trimethoxysilyl)-propyldimethyloctadecyl ammonium chloride as the active ingredient. Another example of a useful antimicrobial agent incorporates 3-(trimethoxysilyl)-propyldimethyltetradecyl ammonium chloride as the active ingredient.

The present invention preferably has the microbiocide function introduced as part of a polymeric film applied to the internal surfaces of the equipment. The polymeric film is generated in situ using an organosilane precursor which is dispersed using a unique mixture of polymeric wetting agents and can be re-applied or replenished without having to dismantle the machinery. Experiments and measurements have shown that such attached microbiocidal films are robust, durable and provide extensive temporal antimicrobial effects. In part the polymeric film destroys microbes by the surface structure of the coating.

Biomass Conversions

The biomass produced in the current process has a number of uses as outlined above. The biomass produced in reaction chamber C (FIG. 1) has advantageously been sanitized and reduced in volume. Importantly, the steam processing has disrupted the structure of the organic materials so that the cellulose and other constituents are opened and more readily available for downstream processing. The biomass is essentially a source of cellulose that has been treated so that the cellulose is readily available for further processing, such as to form bio-fuel, bio-alcohols or the like.

Fermentation of Biomass to Fuel Alcohol

The production of alcohols by fermentation of a biomass is one of the oldest biotechnological methods. Also the use of fermentative recovered ethanol as a source of energy has been known for a long time, but has not been commercially used due to costs being higher in comparison to the recovery of petroleum in the past. The possible use of bio-ethanol has new importance as source of energy as supplies of petroleum become more scarce and the cost increases.

The development of renewable biofuels is an international priority motivated by both economic and environmental concerns, including reduction of greenhouse gas emissions, enhancement of the domestic fuel supply and maintenance of the rural economy. The use of microbes to produce biofuel materials is a particularly attractive way to produce the biofuels, particularly when the microbes do so by utilising waste products generated by other processes.

Gasification of Biomass

Synthesis gas ("syngas") was first developed as a major by-product of the gasification of coal and of carbonaceous materials such as agricultural crops and residues. In contrast to combustion, which produces primarily carbon dioxide and water, gasification is carried out under a high fuel to oxygen ratio and produces largely hydrogen gas ($H_2$) and carbon monoxide (CO). Thus, syngas is composed largely of $H_2$ and CO, together with smaller amounts of $CO_2$ and other gases. Syngas can be directly used as a low-grade fuel or as the feed for fuel cells. Alternatively, it can be used in catalytic processes to generate a wide variety of useful chemical products, such as methane, methanol and formaldehyde. The biomass of the present invention is eminently suitable as the feed for forming syngas.

Anaerobic microorganisms such as acetogenic bacteria offer a viable route to convert syngas to useful products, in particular to liquid biofuels such as bio-ethanol and bio-diesel. Such bacteria catalyze the conversion of syngas with higher specificity, higher yields and lower energy costs than can be attained using chemical processes. Several microorganisms capable of producing biofuels from waste gases and other substrates have been identified.

For example, three strains of acetogens have been described for use in the production of liquid fuels from syngas: *Butyribacterium methylotrophicum* (Grethlein et al., 1990; Jain et al., 1994b); *Clostridium* autoethanogenum (Abrini et al., 1994); *Clostridium ljungdahlii* (Arora et al, 1995; Barik et al., 1988; Barik et al. 1990; and Tanner et al., 1993). *Clostridium ljungdahlii* and *Clostridium autoethanogenum* are known to convert carbon monoxide to ethanol. US patent application No. 2007/275447 describes *Clostridium carboxidivorans*, ATCC BAA-624, "P7" capable of synthesizing, from waste gases, products which are useful as biofuel, in particular, P7 can convert carbon monoxide to ethanol.

Acid Hydrolysis of Biomass for Alcohol Production

The biomass typically contains two basic constituents, carbohydrates and lignin. The carbohydrate content of the biomass consists of cellulose and hemicellulose, both polysaccharides. Both cellulose and hemicellulose may be converted to simple sugars, particularly hexose (including glucose, fructose, mannose and galactose) and pentose (including xylose and arabinose) sugars. The hexose sugars are conventionally fermented to form ethanol, and the pentose sugars are now fermentable utilizing a variety of commercially available microorganism strains, including (but not limited to) the yeast Pachysolen tannophilus NRRL Y-2460, the yeast *Candida tropicalis* ATCC 1369, Fursarium strains of fungus developed by Argone National Laboratory, and *Bacillus Macerans* developed by The University of California at Berkley, and Lawrence Berkley Laboratory. Ethanol, butanol, 2,3-butanediol, are typical alcohols produced. All are practical and versatile alcohols for transportation usages since high percentages can be mixed with gasoline without significant engine modifications, and they have relatively few corrosive effects on vehicle fuel systems.

Fuel alcohols can be produced from biomass containing carbohydrate and lignin with net energy production. That is, alcohol can be produced from biomass without the addition of energy from any external source, the introduced biomass itself providing both the raw material for the ethanol and the energy for all process steps. In fact, depending upon the particular operational steps and parameters, more energy than is necessary for all of the process steps may be produced, and may be sold either as steam or electricity.

Thus, alcohol can be produced from biomass containing carbohydrate and lignin by particlizing and slurrying the biomass and then continuously subjecting the biomass to acid hydrolysis. The acid hydrolysis is performed at temperature, acid concentration, and residence time conditions sufficient to effect hydrolysis of the hemicellulose in the biomass to effect separation of pentose and hexose sugars therefrom into a hydrolysate having insufficient furfural to substantially inhibit fermentation microorganism growth, while not substantially hydrolyzing the cellulose in the biomass. Then fermentation of the pentose and hexose sugars in the hydrolysate is effected, such as by exposing them, under proper environmental conditions, to the yeast Pachysolen tannophilus NRRL Y-2460, Fursarium strains of fungus, and *Bacillus Macerans*, or the like, and then alcohol is produced from the fermented pentose and hexose sugars through normal processing (e.g. distillation).

In some circumstances, it can be desirable to direct hydrolysis toward hemicellulose breakdown, while not being concerned with cellulose breakdown, in order to minimize furfural production. This can have the benefit that energy consumption by the process is minimized, and the remaining biomass (including lignin and cellulose) remaining after acid hydrolysis of the hemicellulose can be burned to produce energy for all of the process steps, as well as additional energy for other purposes. It is necessary to minimize production of inhibitors, such as furfural, since small concentrations of some inhibitors can adversely affect the growth rate, or kill, the fermentation microorganisms.

Acid hydrolysis preferably is normally practiced with an acid concentration of about 2 to 70% by volume (preferably sulphuric acid), and the hydrolysis temperature is about 120° C. or less. The residence time in the acid hydrolysis treatment is about 1 to 3 hours, and the treated biomass slurry has a biomass solids to liquid ratio of about 20/100 to 40/100 on a volume basis. The particle size of the biomass is about 1-4 mm.

An alternative method of treating biomass having fermentable material comprises the following steps: slurried biomass is pumped to an upright acid hydrolysis vessel, with the biomass preferably having an average particulate size of 1-4 mm. Acid hydrolysis of the biomass is continuously effected in the vessel at a temperature of about 120° C. or less to provide a hydrolysate. A first portion of the hydrolysate is passed to an ultimate destination for fermentation thereof, and a second portion of the hydrolysate is passed to the slurrying conduit to effect slurrying of the biomass. The biomass in the vessel is washed after acid hydrolysis thereof by introducing a stream of hot wash water into a top portion of the vessel. Hydrolyzed and washed biomass is withdrawn from the top of the vessel and dewatered. Water from the dewatering of the biomass is passed to the stream of wash water introduced into the vessel.

The hydrolysate preferably is acted upon by neutralizing it with lime, clarifying it, and then passing it to a conventional fermentation vessel. After fermentation, the "beer" is passed on to a yeast separation stage and then ultimately to conventional distillation towers where ethanol, butanol, 2,3-butanediol, and/or other alcohols, are produced. After dewatering the biomass is passed to a furnace, along with products from the yeast separation, to produce steam. The volume of steam produced is sufficient to supply the steam necessary for the distillation towers, for steaming of the biomass in the surge bin, for heating the wash water, and for running all necessary pumps, mixers, and the like. Additionally, there should be sufficient energy left over so that the entire facility is a net energy producer, producing steam or electricity in addition to the alcohol, without the introduction of energy from an external source (aside from the biomass itself).

Biomass may be converted to alcohol using ultrasonic energy. US patent application No. 2008/044891 (FC STONE CARBON LLC) entitled "Biomass conversion to alcohol using ultrasonic energy" describes a method comprising applying ultrasonic energy to a biomass to alcohol production process, such as an ethanol production process. The process employs ultrasonic energy as the only means of pretreatment, or additionally employs a concentrated acid hydrolysis pretreatment, or a hydrothermal or chemical pretreatment, followed by an enzymatic hydrolysis step or a simultaneous enzymatic hydrolysis and saccharification step.

Microwave Catalytic Biomass

Chinese patent publication CN 100999676 (Anhui Univ of Tech) describes microwave catalytic biomass cracking process for preparing biological oil with rich acetone alcohol features using sodium carbonate as catalyst, silicon carbide as microwave absorbing medium, microwave source as heat source for cracking biomass, and ice water mixture for cooling volatile component to obtain biological oil with rich acetone alcohol. By means of the unique temperature effect of microwave in a biomass particle and the unique catalyzing effect of sodium carbonate in cracking biomass, the process realizes the creation of acetone alcohol in high selectivity.

Production of Butanol

The fermentative production of butanol is also well known. International patent publication WO 2008/025522 (Bayer Technology Services GmbH) relates to a method of producing bioalcohol. In particular ethanol or butanol, from biomass, in which the biomass is comminuted, the remaining biomass is fed to a fermentation and the alcohol is obtained from the product of the fermentation, insoluble components and/or non-fermentable sugars being separated off from the biomass before the fermentation and/or yeast and bacteria are separated off after the fermentation.

The Use of Biomass in Fuel Cells

The electric power industry has generally been looking toward the use of fuel cells in relatively large electrical power generating applications. Power generation by fuel cells offers the advantages of high efficiency and low environmental emissions. Thus, fuel cells may offer a more economical means of power production than other existing power producing technologies.

Molten carbonate fuel cells and solid oxide fuel cells are well suited for using heated gas streams and, thus, show great promise in industrial power generation applications. Biomass gasifiers can be used as source for the feed suitable for use in these fuel cells. As described above, the gases required as fuel cell feed are readily obtainable from the gasification of the biomass of the present invention.

Greater efficiency in conventional fuel cells may be obtained through integration with biomass gasifiers, for example, a combined gasifier and fuel cell system wherein the gas stream travels from the gasifier through an external carbon dioxide separator. US patent application No. 2002/194782 (Paisley) describes an integrated biomass gasification and fuel cell system wherein the electrochemical reaction in the fuel cell is effected by providing the reactant gases from a gasifier. Fuel gas from the gasifier is directed to the anode of the fuel cell and at least a portion of the exhaust gas from the anode is directed to a combustor. The portion of the exhaust gas from the anode is then combusted to recover residual energy to increase the overall efficiency of integrated biomass gasification and fuel cell system. Also, the oxidant gas from the combustor may be directed to the cathode of the fuel cell. U.S. Pat. No. 5,736,026 (Energy Res Corp) entitled "Biomass-fuel cell cogeneration apparatus and method" describes the integrated ethanol manufacturing by fermentation of biomass, with an electrical fuel cell generator of electrical and heat energy, the cogeneration including use by the fuel cell of the alcohol, and of the carbon dioxide from the fermentation, which increases the generation of energy, and use by the alcohol manufacturing of the heat and electrical energy from the fuel cell, which increases the fuel manufacture.

It is shown from the foregoing description, that the biomass produced by the present invention can be used in a wide variety of ways. Normally, a particular plant will concentrate on a particular one of these downstream processes, e.g. generating electricity from a fuel cell, or the production of biofuels and bio-alcohols. The skilled person may implement this using one of the techniques described or referenced, or other techniques known in the art or as may be developed.

Summary

In this document, the term ambient pressure is used to define the pressure in the vessel 30 when the vessel is not sealed to gas flow. The pressure in the vessel will thus normally be atmospheric pressure or whatever the prevailing pressure is around the plant. The pressure within the vessel may be slightly higher than the pressure around the plant due to the steam injection even without the vessel being sealed. The term ambient temperature is used in this document to refer to the temperature surrounding the plant which will vary due to location, season and general weather conditions. Cellulose material generally refers to cellulose and hemicellulose unless the context clearly indicates differently.

Generally, this invention relates to a process and apparatus for recycling municipal domestic waste comprises subjecting the waste to steam at 150° C.-200°. After steam treatment, the resultant material is separated into constituent parts and biomass and/or plastics subjected to further treatment. The steam treatment advantageously sanitizes the treated material and significantly reduces the volume thereof. Importantly, the steam treatment disrupts the cellulose and other organic materials so that the fibres are open allowing the steam treated biomass to be more easily converted to bio-fuel, bio-alcohols, etc. The further treatment preferably produces bio-ethanol from the biomass and diesel from the plastics. As an alternative, some or all of the biomass may be gasified in order to produce hydrogen which may, in turn be fed to a fuel cell to produce an electrical output.

The invention claimed is:

1. An apparatus for continuously treating solid waste material comprising:
   a) a non-pressurized vessel, wherein the non-pressurized vessel is a vessel that operates at a pressure under 2 bar, with an inlet for waste material to be introduced at a predetermined rate so that, in use, the waste material only fills the non-pressurized vessel to a known fill level, the vessel including,
      i) an outlet for treated waste;
      ii) conveyor means for transferring treated waste material at a predetermined rate to the outlet such that the known fill level is maintained during operation of the apparatus, and
      iii) a plurality of steam inlets fixed at the non-pressurized vessel for selectively injecting steam in to the interior of said non-pressurized vessel, the interior of the non-pressurized vessel comprising a first zone and a second zone wherein, in use, the first zone is mainly filled with waste material and the second zone is largely empty of waste material;
   b) a drive arranged to rotate the non-pressurized vessel and thus move the steam inlets between the first zone and the second zone such that only some of the steam inlets are in said first zone at any time;

c) a distributor valve for directing steam from a steam generator to the steam inlets, said distributor valve comprising a valve body having an inlet opening fluidly connectable to the steam generator and a plurality of outlet openings fluidly connectable to the steam inlets, wherein the valve is arranged so that at any time at least one of the outlet openings is fluidly disconnected from the inlet opening, whereby steam is supplied only to at least one steam inlet in the first zone of the vessel interior; and d) heating means for heating and/or maintaining the temperature of the interior of the non-pressurized vessel to a temperature of 150° C. to 200° C., the heating means consisting of means for heating of air at the non-pressurized vessel.

2. The apparatus of claim 1, wherein the outlet is connected to a sorting chamber where the treated waste material is separated into plastics, ferrous metals, non-ferrous metals and biomass of cellulose material.

3. The apparatus of claim 1, wherein the biomass is transferred to a hyperbaric engine or a fuel cell or to a conversion unit for converting the biomass into biodiesel or an organic alcohol, such as bio-ethanol or bio-butanol, or an aviation fuel.

4. The apparatus of claim 3, wherein the apparatus further includes electrical generators powered by the biodiesel or organic alcohol.

5. The apparatus of claim 1, wherein the inlet opening of the distributor valve is arranged to be fluidly connected to only one outlet opening of the distributor valve at a time.

6. The apparatus of claim 1, wherein the inlet opening is in an inlet manifold of the distributor valve, with a fluid connection extending in an axial direction through a rotatable valve chamber of the distributor valve to the valve body.

7. The apparatus of claim 6, wherein the rotatable valve chamber has further includes a steam feed for supplying steam to a heating jacket and a condensate return for receiving condensate from the heating jacket, and the steam feed is fluidly connected to a steam line in the inlet manifold and the condensate return is fluidly connected to a return line in the inlet manifold.

8. The apparatus of claim 6, wherein the inlet manifold is non-rotatable.

9. A method for treating waste material comprising the steps of:

a) inputting particulate waste material into the non-pressurized vessel of claim 1, b) heating via the heating means and maintaining the interior of the non-pressurized vessel at a temperature of between 150° C. and 200° C., and c) treating the particulate waste material with steam at a temperature of 150° C. and 200° C., wherein the steam is injected only in to the particulate waste material.

10. The method of claim 9, wherein the method is a continuous method with waste material being input at the inlet of the non-pressurized vessel and treated waste material being output at the outlet of the non-pressurized vessel.

11. The method of claim 9, wherein the treated waste material comprises a biomass of cellulose, plastics, ferrous metals and non-ferrous metals.

* * * * *